United States Patent
Ponjavić

(10) Patent No.: US 12,090,236 B2
(45) Date of Patent: Sep. 17, 2024

(54) SMART DEVICE AND METHOD FOR SAFE DISPOSAL OF INFECTIOUS MEDICAL WASTE USING UV LIGHT

(71) Applicant: Katarína Ponjavić, eŽepče (BA)

(72) Inventor: Katarína Ponjavić, eŽepče (BA)

( * ) Notice: Subject to any disclaimer, the term of this patent is extended or adjusted under 35 U.S.C. 154(b) by 0 days.

(21) Appl. No.: 17/924,658

(22) PCT Filed: May 7, 2021

(86) PCT No.: PCT/BA2021/000003
§ 371 (c)(1),
(2) Date: Nov. 10, 2022

(87) PCT Pub. No.: WO2021/226680
PCT Pub. Date: Nov. 18, 2021

(65) Prior Publication Data
US 2023/0173114 A1    Jun. 8, 2023

(30) Foreign Application Priority Data

May 11, 2020    (BA) .............................. BAP 203357

(51) Int. Cl.
*A61L 2/00*     (2006.01)
*A61L 2/24*     (2006.01)
*A61L 2/26*     (2006.01)

(52) U.S. Cl.
CPC ............... *A61L 2/0047* (2013.01); *A61L 2/24* (2013.01); *A61L 2/26* (2013.01); *A61L 2202/14* (2013.01)

(58) Field of Classification Search
CPC ............ A61L 2/0047; A61L 2/24; A61L 2/26; A61L 2202/14
See application file for complete search history.

(56) References Cited

U.S. PATENT DOCUMENTS 5,348,235 A * 9/1994 Pappas .................... A61L 11/00
241/606

FOREIGN PATENT DOCUMENTS

| CN | 108045812 A | 5/2018 |
| CN | 109481794 A | 3/2019 |
| WO | 2004071667 A1 | 8/2004 |

OTHER PUBLICATIONS

International Search Report for application PCT/BA2021/000003 mailed on Oct. 5, 2021.

* cited by examiner

*Primary Examiner* — Sean E Conley
(74) *Attorney, Agent, or Firm* — NIXON & VANDERHYE

(57) ABSTRACT

Efficient and adequate disposal of medical infectious waste is proportional to the reduction of the spread of infectious diseases and the disease itself among humans. The essence of this invention is that infectious medical waste is in a timely, fast, efficient, simple, and environmentally friendly safely disposed of and turned into inert-municipal waste. Previous methods and devices for the disposal of infectious medical waste involved long-term procedures for the collection, sorting and storage of infectious medical waste, which increases the risk of secondary infections. This invention skips the process of collecting, sorting and storing medical infectious waste, and the entire process in the invention takes place in three unbreakable phases whose end product is municipal-inert waste. It is important to emphasize that with this invention, even the smallest amount of infectious medical waste will be disposed of immediately in an appropriate manner. And as a result, a maximum control over all medical infectious waste is achieved.

13 Claims, 1 Drawing Sheet

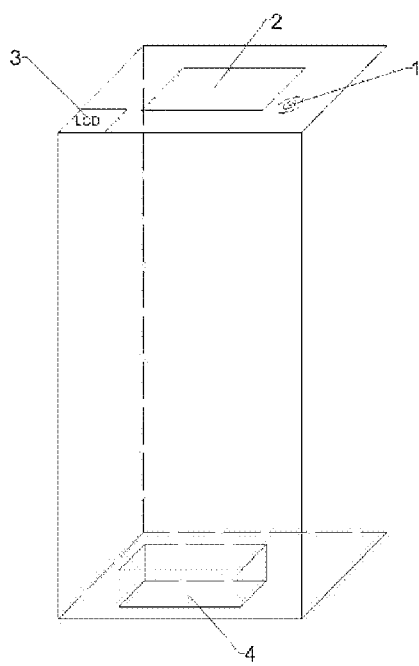
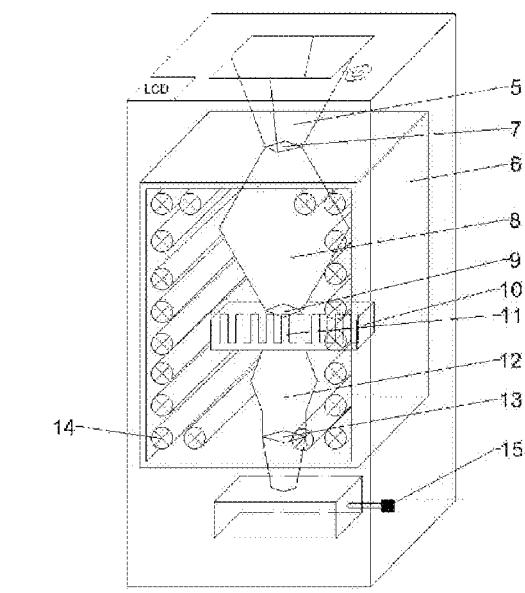
Fig. 1
Fig. 2

SMART DEVICE AND METHOD FOR SAFE DISPOSAL OF INFECTIOUS MEDICAL WASTE USING UV LIGHT

TECHNICAL FIELD

The present invention relates to a category of methods for the disposal of medical waste, and according to the International Classification (ICP) is classified as: B09B 3/0075, as well as to a category of devices for disinfecting or sterilizing materials or objects, and according to the International Classification (ICP) as: A61L 2202/00.

Technical Problem

Infectious and potentially infectious waste makes up the most dangerous and largest part of medical waste. Such waste must be treated in a timely manner and safely disposed of in an adequate manner. Nowadays, we are witnessing a catastrophe that can be caused by the uncontrolled spread of just one virus in the environment. The fact is that the safe disposal of infectious waste requires huge amounts of money and human resources, and in most countries this process is still not under control. This is followed by the fact that, according to estimates, around 12 billion doses of drugs are administered by injections in the world. Improper and untimely disposal of infected needles and syringes pose a high risk of unintentional injury to an infected object during the process of sorting and collecting infectious waste among medical and technical personnel. In addition to the development of infection, improperly and untimely disposed of infected needles and syringes create the possibility of their reuse, and the danger is also posed by rodents, insects and other animals that most often become passive vectors of pathogenic microorganisms in the environment.

PRIOR ART

The current disposal of medical waste is done in such a way that medical waste at the place of origin is collected in simple packaging that, with its characteristics, facilitates further sorting. After sorting the medical waste, the infectious waste is transported to the place of secondary storage. Infectious waste is pre-treated with various disinfection and sterilization procedures. Such devices must bring infectious waste into a state where it is sufficiently sterile so that it is not dangerous to the environment and must not be a potential source of infection. According to actual laws, the storage of infectious waste without treatment may last for a maximum of eight days. These procedures are followed by the process of crushing infectious waste, which must reduce the volume of the waste by at least 75%, and make infectious waste unrecognizable. Such hygienically harmless waste may be treated as inert municipal waste. There are already devices on the market that disinfect waste by ultraviolet radiation, but these devices are mainly used after the process of collecting and sorting large amounts of medical infectious waste, because they are not suitable for small amounts of infectious waste. In this way, a long process of collecting and storing infectious waste is not avoided. This means that infectious waste is not destroyed at the place of origin, and the consequence is a significantly increased risk of further spread of pathogenic microorganisms in the environment.

SUMMARY OF THE INVENTION

The primary object of this method and the invention is to improve existing methods and containers for infectious medical waste. Furthermore, the essence of the method and the invention is that the infectious medical waste is safely disposed of and quickly turned into inert-municipal waste in a fast, efficient, simple, and environmentally friendly way.

The present invention represents a new method of disposing of medical infectious waste. The end product is inert-municipal waste.

In relation to previous devices for the disposal of medical infectious waste, the present invention will contain two disinfection chambers, which will result in the maximum destruction of all pathogenic microorganisms. The metal chamber within the invention will prevent the passage of UV rays into the environment. In this way, the use of the invention will be maximally safe for humans. The metal chamber will also allow the creation of the necessary optimal conditions (e.g., optimal temperature, humidity, air composition, etc.) to achieve the most efficient action of UV rays within the invention. According to one scientific research paper, published in NCBI on Feb. 11, 2020; US National Library of Medicine—National Institutes of Health, has proven that VUV lights under certain and controlled conditions in a precisely defined period of time effectively kill pathogenic microorganisms. Based on these facts, the invention will use a combination of previously proven effective UVC lights and VUV lights. This combination with optimal controlled conditions will enable the most efficient disinfection of infectious medical waste. This invention will enable even the smallest amount of infectious waste to be treated immediately, which has not been the case so far. In this way, the operation of the device is not limited according to a certain weight of waste. The invention will also signal via an LCD display when the final waste container is full, so that nurses and other technical staff tasked with monitoring the waste and emptying existing infectious waste containers will be completely relieved of that part of the job. It is important to emphasize that disinfection with UV lights is equally or more economical (depending on additional parameters) compared to other methods and devices, and also the most environmentally friendly of all previous methods.

With medical sharp objects such as needles, the risk of injury to medical and technical staff will be minimized or non-existent. This means that the risk of infection that could result from unintentional injury to infected items by medical and technical staff will also be minimized. It is important to emphasize that there is an increase in the number of infections in the world after stabbing incidents among medical and technical staff. This means that the need for additional vaccinations against various types of diseases also increases.

The risk of reusing potentially infectious medical supplies will be minimized. It also means that passive transmission of infectious diseases through animals will be prevented.

This device and method skips the process of collecting, sorting and storing medical infectious waste, which is automatically reducing the necessary costs of all public medical institutions. This invention and method will greatly facilitate the development of various plans of the government institutions for the disposal and control of medical infectious waste. This means that the present invention will enable maximum control over medical infectious waste. Finally, it is important to emphasize that the medical infectious waste disposal system is an integral part of the long-term health care of humanity and the environment.

One of the key advantages of this method and the invention is that the exposure to potential infection from infection will be greatly reduced in the sense that the medical infectious waste at the place of origin will be immediately and adequately disposed of and converted into municipal inert waste. For a better understanding, we will give one example. Take, for example, a patient suffering from HIV. That patient came to the dentist to treat the tooth. He may not have intentionally or unintentionally told the doctor that he was suffering from some contagious disease. After the doctor has applied anesthesia to the patient, he is obliged to adequately dispose of the used needle and syringe in the container for infectious waste. When disposing of such waste, incidents of self-harm often occur when the protective cap is placed on the needle. This is when the infection spreads, which means that the doctor can become infected with the virus that the patient is carrying.

Furthermore, such an infected needle and syringe, before being processed, pass through the hands of many more people. According to the actual laws, such untreated waste can be stored for up to 8 days. This invention bypasses this procedure and allows the doctor to immediately insert a needle and syringe into the invention without placing a protective cap and to treat the infected needle after a short period of time, environmentally friendly, and converted into municipal inert waste.

BRIEF DESCRIPTION OF THE DRAWINGS

The accompanying drawings, which are incorporated in and constitute a part of the specification, illustrate the best mode for carrying out the method and the invention discussed so far in order to explain the essence of the invention.

FIG. 1 is a spatial view of the outer part of the invention.
FIG. 2 is a spatial view of the exterior and interior of the invention.

List of used labels:
1—switch for opening of the lid
2—cover
3—LCD display
4—final waste container
5—inlet pipe
6—metal chamber
7—inlet pipe opening
8—first disinfection chamber
9—opening of the first disinfection chamber
10—chamber in which the grinding/crushing system is located
11—grinding/crushing machine
12—second disinfection chamber
13—opening of the second disinfection chamber
14—UV lamps
15—vacuum device

DETAILED DESCRIPTION OF AT LEAST ONE OF THE EMBODIMENTS OF THE INVENTION

FIG. 1 shows an external view of the invention. It includes the following parts: lid opening switch (1), lid (2), LCD display (3) and waste bin (4). The lid opening switch (1) is there to facilitate access to the disposal of medical infectious waste in the invention. Its purpose lies in the fact that the lid (2) of the invention must be closed at all times for safety reasons except at the time of insertion of the medical infectious waste. That is, the cover (2) must be closed at all times except when the lid opening switch (1) is pressed. In this way, a physical barrier is provided by means of a lid (2) from the inlet pipe (5) in which the medical infectious waste will be located. This is necessary to control the medical infectious waste itself. If any obstruction is found in the space between the open lid (2) and the infectious medical waste container (4) by means of the sensor, the lid (2) will be opened or the closing will be suspended until the space is free for total closure.

The necessity of the LCD display (3) is because it will be a indicator of the following items: volume of medical infectious waste in the first disinfection chamber (8), percentage of battery of the invention, volume of municipal inert waste, possible errors and other technical specifications.

The necessity of the final waste container (4) is reflected in that this container will contain fully treated medical infectious waste, i.e. municipal-inert waste. When the container is filled to the maximum volume of municipal inert waste, the sensor will signal this and the LCD display (3) will show that the municipal inert waste is ready for further disposal.

FIG. 2 shows the interior of the invention as well as the arrangement of the associated elements in the smart device. The inner part of the invention includes the following parts: inlet pipe (5), metal chamber (6), inlet pipe opening (7), first disinfection chamber (8), opening of the first disinfection chamber (9), chamber in which the grinding/shredding/crushing system is located (10), grinding/shredding/crushing machine (11), second disinfection chamber (12), opening of second disinfection chamber (13), UV lamps (14) and vacuum device (15).

The inlet tube (5) is the place of disposal of infectious medical waste. Pressing the lid opening switch (1) automatically opens the cover (2) on the smart device.

Infectious medical waste is inserted into the inlet pipe (5) of the device which falls on the lid that fills the opening of the inlet pipe (7) located on the upper part of the first disinfection chamber (8). After a certain time, the cover on the smart device (2) closes automatically. After closing the lid (2) on the smart device, a few seconds later, the lid opens which fills the opening of the inlet tube (7) which allows the inserted infectious medical waste to slide into the first disinfection chamber (8). A few seconds later, the cover that fills the opening of the inlet pipe (7) closes automatically, which means that the inlet pipe (5) is emptied. This prevents any secondary contact of people with medical infectious waste, as well as the accumulation of medical infectious waste in the inlet pipe (5).

The necessity of a metal chamber (6) is manifested in the fact that it represents the main form of protection against UV light for people who may be in the vicinity of the invention. The metal chamber (6) will prevent the passage of UV rays into the environment. In this way, the use of the invention will be maximally safe for humans. The metal chamber (6) will also allow the creation of the necessary optimal conditions (e.g., optimal temperature, humidity, air composition, etc.) to achieve the most efficient action of UV rays within the invention.

The cover that fills the opening of the inlet pipe (7) has the role of preventing any secondary contact of people with medical infectious waste. The cover that fills the opening of the inlet pipe (7) opens or closes automatically at the set time.

The first disinfection chamber (8) has the role of collecting medical infectious waste up to a certain amount or volume. After closing the cover that fills the opening of the inlet pipe (7), a few seconds later, all UV lamps (14) are automatically turned on and the first phase of disinfection begins. The UV lamps (14) are lit for a certain period of time and then turn off automatically. This procedure is repeated until a sufficient amount or volume of infectious waste is collected. When a sufficient amount or volume of infectious waste is collected, the lid that fills the opening of the first disinfection chamber (9) is automatically opened, and at the same time a grinding/shredding/crushing machine (11) is put into operation (one of these methods is used depending on the type of infectious waste). Infectious medical waste gradually falls into the grinding/shredding/crushing chamber (10) where the infectious waste is shredded/grounded or crushed to the optimum intended size.

The opening of the first disinfection chamber (9) has the role of keeping in the closed position the intended amount or volume of infectious medical waste that would be sufficient to activate the grinding/shredding/crushing machine (11). The opening of the first disinfection chamber (9) is opened by means of sensors located inside the first disinfection chamber (8). When a certain volume of infectious medical waste is filled in the first disinfection chamber (8), the sensors report that the condition for starting the grinding/shredding/crushing machine (11) is met, and at the same time the UV lamps (14) light up and the lid opens automatically which is contained in the opening of the first disinfection chamber (9). Through the opening of the first disinfection chamber (9), the infectious waste falls into the space of the grinding/shredding/crushing chamber (10). Infectious waste gradually enters the grinding/shredding/crushing machine (11) where it is prepared for final UV treatment. After switching off the grinding/shredding/crushing machine (11), the opening of the first disinfection chamber (9) closes automatically.

The grinding/crushing/crushing chamber (10) has the role of gradually accepting the infectious medical waste from the first disinfection chamber (8) and to prevent the grinding/crushing/crushing machine (11) from being backfilled.

The grinding/shredding/crushing machine (11) has the role of grinding, shredding or crushing infectious waste, depending on the type of infectious waste. The original intention was to apply one of these methods of treating infectious medical waste, but it could also be a combination of several systems that would encompass all three operations. There are such machines on the market that meet the requirements of the present invention, both in power and size.

The second disinfection chamber (12) has the task of bringing the infectious medical waste into a state of municipal internal waste ready for further disposal. Thus, shredded infectious medical waste gradually falls into the second disinfection chamber (12). After activating the grinding/shredding/crushing machine (11), the UV lamps (14) are lit. The grinding/shredding/crushing machine (11) switches off automatically (after the load has stopped) and the UV lamps (14) remain on until the infectious medical waste becomes a harmless municipal inert waste. The duration of action of UV lamps (14), according to expert research, should last approximately 30 minutes. At the same time, systems for humidity, temperature and air quality are activated, in order to enable the most efficient action of UV radiation in the process.

The lid that fills the opening of the second disinfection chamber (13) is located at the very bottom of the second disinfection chamber (12), and its purpose is to keep the shredded infectious medical waste in the second disinfection chamber (12) for a certain period of time to disinfect medical infectious waste. sterilizes. After the expiration of this time period, the lid that fills the opening of the second disinfection chamber (13) is automatically opened, and the crushed internal municipal waste passes through the opening and enters the vacuum-plastic bag. When all the shredded internal municipal waste from the second disinfection chamber (12) enters the plastic vacuum bag, the lid that fills the opening of the second disinfection chamber (13) is automatically closed and the internal municipal waste is ready for vacuum packaging.

UV lamps (14) are located inside the smart device, and are attached to the metal chamber (6), and properly arranged in a way that allows the most efficient action of UV rays. The efficient action of UV rays means that pathogenic microorganisms will not have any possibility of survival, which aims at this smart device, which is to bring infectious medical waste into a state that is harmless to humans and the environment, or acceptable inert municipal waste. In the present invention, UV lamps (14) emitting ultraviolet radiation at 254 nm wavelength (UVC lamps) and lamps emitting ultraviolet radiation at 185 nm wavelength (VUV lamps) will be used.

The vacuum device (15) has the function of vacuuming the internal municipal waste so that the internal municipal waste is suitable for further disposal. The vacuuming procedure is as follows: Upon completion of the UV disinfection procedure, the lid that fills the opening of the second disinfection chamber (13) is automatically opened and the inert waste enters the vacuum bag. After the vacuum bags are filled to the maximum, the inert medical waste vacuum device (15) is activated. The vacuum bag is disposed of in the final waste container (4) and a new empty vacuum bag is automatically placed in its place. When the final waste container (4) is completely filled with vacuum bags, the LCD display (3) signals that the final waste container (4) needs to be emptied and that the inert waste is ready for further disposal.

The present invention will be powered by electricity and it is important to emphasize that all additional electrical parts already invented, which represent necessary parts of the present invention. Also, the dimensions of the device will be adjusted to the needs of the market or end users. This means that for users who produce smaller quantities of medical infectious waste per day, smaller devices will be constructed with dimensions and capacity for receiving quantities of infectious waste, and that for users who produce larger quantities of medical infectious waste per day, larger devices can be constructed and manufactured.

In the manner described above, the invention provides a practical, safe, useful and durable device comprising significant improvements and advances over existing inventions to date. It will be apparent to those skilled in the prior art that a number of changes may be made to the present methods and packaging for the safe disposal of medical infectious waste according to the present invention and method, without departing from the scope and spirit of the present invention and method.

The invention claimed is:

1. A smart device for the safe disposal of medical infectious waste, the smart device consisting of:
   executive and control components; and
   basic parts including
      an outer part of the smart device consisting of:
         lid,
         one of a switch configured to open the first lid after being pressed, and an automatic shutter configured to close after the medical infectious waste is inserted into the smart device,
         a liquid crystal display (LCD) configured to show a state indicative of an operation of the smart device, and
         a final waste container, and an inner part of the smart device consisting of:
a smaller upper part in which an inlet pipe is located, and
a larger lower part that is a metal chamber containing:
a first disinfection chamber,
an opening of the inlet pipe configured to be covered with an inlet pipe protective cover, which is a connection between the inlet pipe and the first disinfection chamber,
an opening of the first disinfection chamber configured to be covered with a first disinfection chamber protective cover, which is a connection between the first disinfection chamber and a grinding chamber in which a grinding/shredding/crushing system is located, a grinding/shredding/crushing machine being provided inside the second chamber,
a second disinfection chamber having an opening configured to be covered with a second disinfection chamber protective cover, the opening of the second disinfection chamber being configured to provide a connection between the second disinfection chamber and the final container for waste,
a plurality of ultraviolet (UV) lamps configured to fill the entire interior of the metal chamber with UV light, and
a plurality of vacuum devices.

2. A method for safe disposal of infectious medical waste using the device according to claim 1, the method comprising:
preventing the UV light from entering the environment by containing the UV light by the metal chamber.

3. The method for safe disposal of infectious medical waste using the device according to claim 2, wherein the metal chamber creates one or more of an optimum temperature, an optimum humidity, and air composition to efficiently operate UV rays.

4. A method for safe disposal of infectious medical waste using the device according to claim 1, the method comprising:
receiving, by the inlet pipe, the medical infectious waste after opening the first lid when the switch is pressed, whereby and after removing the medical infectious waste, the first lid closes automatically.

5. The method for safe disposal of infectious medical waste using the device according to claim 4, wherein, after the waste is received in the inlet pipe and the lid automatically closes, the medical infectious waste is prevented from contacting a user, the medical infectious waste within the inlet pipe falling on the inlet pipe protective cover which closes the opening of the inlet pipe, causing the first lid to automatically open and the waste from the inlet pipe to slide into the first disinfection chamber, and thereafter automatically close the opening of the inlet pipe.

6. The method for safe disposal of infectious medical waste using the device according to claim 5, further comprising:
after the waste slides into the first disinfection chamber, automatically lighting the UV lamps inside the device to perform a first disinfection and sterilization phase; and
when there is insufficient waste in the device for further processing, programming the UV lamps to shut off after a certain period of time, until new infectious waste is inserted.

7. A method for safe disposal of infectious medical waste using the device according to claim 1, the method comprising:
collecting waste of about 50%-85% of the volume of the first disinfection chamber which was exposed to UV rays for a certain period of time, the waste perishes in the first disinfection chamber in which the grinding/shredding/crushing system is located through the opening of the first disinfection chamber.

8. The method for safe disposal of infectious medical waste using the device according to claim 7, further comprising, after the waste has perished in the first disinfection chamber, starting the grinding/shredding/crushing system,
wherein the waste is grounded/shredded/crushed to a size that achieves efficiency of UV lights for a final disinfection of the waste in the second disinfection chamber.

9. The method for safe disposal of infectious medical waste using the device according to claim 8, wherein, during operation of the grinding/shredding/crushing system, the shredded waste gradually falls into the second disinfection chamber through the opening connecting the grinding chamber and the second disinfection chamber.

10. A method for safe disposal of infectious medical waste using the device according to claim 1,
after a decay of the waste in the second disinfection chamber, performing a final disinfection of the waste using UV lights for a specific period of time; and
after the waste is exposed to the UV light for the specific period of time and when the final disinfection is complete, receiving the waste through the opening of the second disinfection chamber into the final waste container.

11. A method for safe disposal of infectious medical waste using the device according to claim 1, the method comprising:
disinfecting and sterilizing the shredded medical infectious waste, the second disinfection chamber protective cover that covers the opening of the second disinfection chamber being located at the very bottom of the second disinfection chamber and the shredded keeping infectious medical waste in the second disinfection chamber for a specific period of time;
automatically opening the second disinfection chamber protective cover after the specific time period expires, the shredded internal waste passing through the opening and entering a plastic vacuum bag; and
when all the shredded internal waste from the second disinfection chamber enters the plastic vacuum bag, automatically closing the second disinfection chamber protective cover that covers the opening of the second disinfection chamber such that the shredded internal waste is ready for vacuum packaging.

12. A method for the safe disposal of infectious medical waste using the device according to claim 1, the method comprising :
after at least one vacuum bag that is disposed in the final waste container into which the waste falls is filled to the maximum, activating a vacuum device of inert medical waste by a sensor;
disposing the at least one full vacuum bag that is in the final waste container; and
replacing the full vacuum bag with a new empty vacuum bag.

13. The method for the safe disposal of infectious medical waste using the device according to claim 12, further comprising:

when the final waste container is filled with at least one vacuum bag containing the inert municipal waste, signaling, by the LCD display, that the final waste container needs to be emptied and that the inert municipal waste is ready for further disposal.

\* \* \* \* \*